United States Patent [19]
Sherva-Parker

[11] Patent Number: 4,781,720
[45] Date of Patent: Nov. 1, 1988

[54] AMPUTATION APPARATUS

[76] Inventor: Carole J. Sherva-Parker, Rt. 1, Box 152, Thief River Falls, Minn. 56701

[21] Appl. No.: 11,160

[22] Filed: Feb. 5, 1987

[51] Int. Cl.4 .............................................. A61F 2/28
[52] U.S. Cl. .................................................... 623/16
[58] Field of Search ................ 623/16, 18, 33–37, 623/27

[56] References Cited

U.S. PATENT DOCUMENTS

| | | | |
|---|---|---|---|
| 3,947,897 | 4/1976 | Owens | 623/27 |
| 4,007,494 | 2/1977 | Sauer | 623/16 |
| 4,158,895 | 6/1979 | Reswich | 623/16 |
| 4,547,912 | 10/1985 | Sherva-Parker | 623/16 |

FOREIGN PATENT DOCUMENTS

| | | | |
|---|---|---|---|
| 3125268 | 1/1983 | Fed. Rep. of Germany | 623/16 |
| 1046920 | 12/1953 | France | 623/16 |
| 1525667 | 9/1978 | United Kingdom | 623/16 |

Primary Examiner—Richard J. Apley
Assistant Examiner—James Prizant
Attorney, Agent, or Firm—Arnold S. Weintraub

[57] ABSTRACT

Disclosed is an internal prosthesis for use with a prosthesis attachable externally to a residual limb having a bone with a free end thereof. The internal prosthesis comprises bone end pressure distributing means disposed completely within the residual limb and open-bottomed bone end containing means attached to the bone end pressure distributing means. In separate embodiments, the bone end pressure distributing means comprises a tubular, mesh sock/sleeve with a central aperture. The open-bottomed end containing means comprises a mesh bone sock/sleeve which surrounds the central aperture and extends up the bone disposed around the aperture and also provided with a reinforced portion. Alternatively, the bone end pressure distributing means comprises a radially extending plate with an central aperture around which is disposed an upwardly extending boss. The bone end containing means comprises an open-ended bone cap which is formed of two sections. The first section comprises a portion of bone pins and the second section comprises a boss with a smaller diameter than the first section.

28 Claims, 4 Drawing Sheets

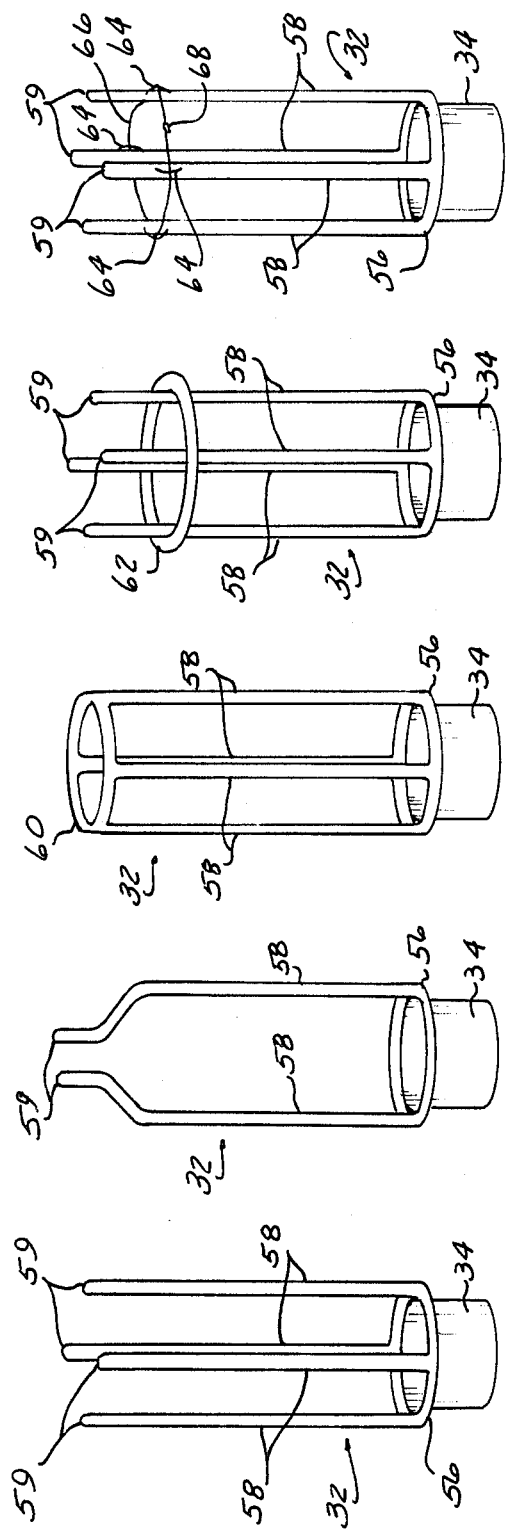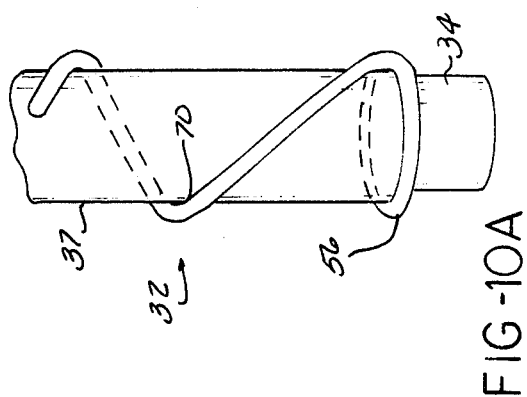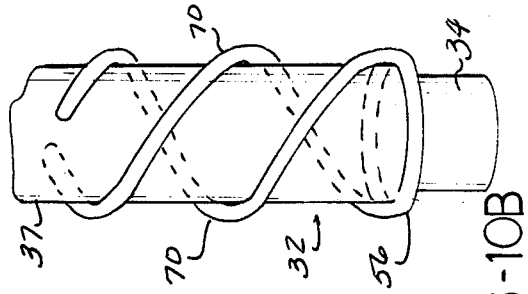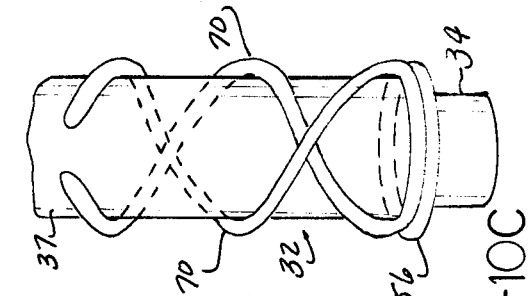

AMPUTATION APPARATUS

BACKGROUND OF THE INVENTION

1. Field of the Invention

This invention relates, in general, to prostheses which are externally attachable to severed or amputated limbs and, more specifically, to apparatus for use in attaching prostheses to the limbs.

2. Description of the Prior Art

It is common to attach a prosthesis or artificial limb externally onto the stump of a limb of an individual which has been amputated or otherwise severed in order to provide a measure of use of the limb to the individual. Specifically, a strap and harness assembly is utilized which engages the stump of the limb. During use of the weight bearing limb, such as a leg or arm, forces are generated which are transmitted through the prosthesis directly to the flesh surrounding the stump. Since it is difficult to insure a secure, non-slip engagement between the prosthesis and the limb, the forces generated during use of the prosthesis create movement of the prosthesis relative to the stump which result in irritation of the flesh surrounding the stump and discomfort to the wearer which makes it difficult, if not impossible, to effectively use the prosthesis in a normal manner.

One solution to the above-listed patents is shown in my U.S. Pat. No. 4,547,912. This patent proposes employing an amputation apparatus comprising two parts. The first part is a cap having an internal cavity for insertion over the bone and an opposed outwardly extending boss. The second part comprises a plate having an internal cavity mountable over the outwardly extending boss of the cap. The plate has a radial extent substantially greater than the radial extent of the cap to define an equal weight distribution surface for internal and external forces over the entire bottom surface of the stump.

While the two piece amputation apparatus constitutes an improvement over the prior art, certain problems may still occur. The bone cap disclosed in U.S. Pat. No. 4,547,912 is comprised of an open top, a bottom and side walls. Because the bottom surface is continuous, the bone end of the an amputated limb over which such a cap is placed is isolated from the tissue of the amputated limb which is wrapped around the plate part of the two-piece assembly. Since the bone within the amputated limb continues to be a living tissue, it would be less likely to suffer deterioration and subsequent withering if it were allowed to be in contact with muscle and skin tissue contained in the amputated limb. Additionally, the problem of slippage between an amputated limb and the prosthesis remains unresolved, since no provision in U.S. Pat. No. 4,547,912 is made for a secure, non-slip attachment.

Thus, it would be desirable to provide an amputation apparatus which overcomes the problems described above for use with a prosthesis attached externally to a severed or amputated limb. It would also be desirable to provide an amputation apparatus which allows the bone end to remain in contact with the other tissue contained in the amputated limb. Finally, it would be desirable to provide an amputation apparatus which may be attached to an external prosthesis in a secure, non-slip manner.

SUMMARY OF THE INVENTION

The present invention is an internal prosthesis for use with a prosthesis attachable externally to a residual limb having a bone with a free end thereof. The internal prosthesis comprises means for distributing pressure from the bone end over the end of the residual limb, the bone end pressure distributing means being disposed completely within the residual limb, and open-bottomed bone end containing means attached to the bone end pressure distributing means. The bone end distributing means may be comprised of a magnetically transmissive or receptive material, in which case it may be easily and securely attached to a correspondingly magnetically transmissive or receptive external prosthesis such as that disclosed in my co-pending application entitled External Prosthesis with Magnetic Field, (U.S. Pat. No. 4,743,264) the disclosure of which is hereby incorporated by reference.

In one embodiment of the internal prosthesis of the instant invention, the bone end pressure distributing means comprises a large, flexible, tubular sock/sleeve sized to fit over the muscle tissue of the residual limb and underneath the skin thereof. The tubular sock/sleeve has a smooth, continuous, reinforced, closed end portion to receive the full force of pressure generated by the free end of the bone. The bone end containing means comprises a bone sock/sleeve sized to fit over the free end of the bone disposed at the center of the reinforced portion and integral therewith, and a means of permanently fastening the bone sock/sleeve to the bone. In the embodiment of the internal prosthesis of the instant invention, the tubular sock/sleeve may further comprise a support ring having a circular piece disposed around the exterior of the bone sock/sleeve adjacent the reinforced portion and an X-shaped cross piece integral with the circular piece and disposed interiorly of the bone sock/sleeve, with the arms of the X extending therethrough. The purpose of the support ring is to provide further support for the bone end and to help distribute the pressure genrated therefrom.

The tubular sock/sleeve may be comprised of a mesh material, and preferably of a metalized, magnetically attractive mesh material. The reinforced portion is preferably comprised of a strengthened mesh material or of a solid material and has a diameter of at least as great as the diameter of the bone.

The bone sock/sleeve component of the internal prosthesis of this embodiment of the present invention may further comprise a reinforced section adjacent and integral with the reinforced portion of the tubular sock/sleeve and extending around a bone sock/sleeve for a distance upwardly from the reinforced portion. A means of permanently fastening the bone sock/sleeve to the bone may be selected from the group consisting of adhesive, screws, clamps, pins, staples, and other combinations thereof. The large, tubular sock/sleeve may be fastened to the muscle tissue and skin of the individual limb by intermittent suture fastening.

In an alternative embodiment of the internal prosthesis of the instant invention, the bone end containing means comprises a cap securable to the end of the bone. The bone cap has an open top and bottom, first and second side portions with the second portion having a smaller diameter than the first portion to define an outwardly extending boss on the cap, and an internal cavity formed in the cap sized to fit externally over the free end of the bone. In this embodiment, the bone end pressure distributing means comprises a plate having top and bottom surfaces, a centrally located aperture formed therein and a boss formed on the top surface, disposed around the aperture, and sized to receive the boss on the bone cap therein. The plate extends radially outward a substantial distance beyond the periphery of the boss to evenly distribute forces from the prosthesis over the end of the residual limb, and is completely disposed therein. The bone end pressure distributing means further comprises support means disposed within the aperture to support the free end of the bone.

In this embodiment of the instant invention, the plate may further comprise a plurality of concentric ribs formed thereon, and/or an upwardly extending rib formed integrally on the perimeter thereof. The purpose of these additional structures is to prevent slippage of the plate with respect to the residual limb when the prosthesis is in place. The plate may be comprised of a bio-compatible, magnetic material, such as metalized ceramic material. Support means disposed within the aperture of the plate may comprise two or more rods joined at their centers with their ends projecting radially outward therefrom and connecting to the plate or the two or more rods may join to sides of the support ring and extend upward and outward thereform. Alternatively, the support means may comprise of a piece of reinforced mesh attached at an edge thereof to the plate.

The first portion of the bone cap is designed to extend upwardly and surround the bone of the amputated limb. The first portion may exhibit a variety of designs. It may be comprised of a first ring and at least two prongs projecting upwardly therefrom, each of the prongs terminating in a tip. Each tip may be inwardly bent to grip the bone more securely. Alternatively, the prongs may integrally terminate in a second ring disposed in parallel and spaced apart relation to the first ring. Alternatively, the first portion may further comprise a second ring disposed around the prongs near the tips thereof. The prongs may each have a guide loop formed on the side thereof opposite the side adjacent the bone and near the tips. The ends of the cable are threaded through the loops to encircle the bone, and an adjustable connector connects the two ends and draws them together, thereby tightening the cable around the bone and securing the cap thereto.

In another bone cap design, the first section may further comprise a ring and at least one spiral projecting upwardly therefrom to encircle the bone. If a plurality of spirals are employed, the spirals may spiral in the same radial direction or in opposite radial directions.

Alternatively, the first section of the bone cap may comprise a mesh sleeve having an open rolled top and an open bottom sized to encircle the bone. The bottom of the mesh sleeve is attached to an internal surface of the second section and is fastened to the bone at the rolled top by staples.

In yet another form, the open top of the mesh sleeve is not rolled. In that case, a plurality of guide loops is provided which are disposed around the periphery of ring. A tunnel is provided which is formed in the mesh encircling the bone adjacent the ring, said tunnel having a plurality of openings formed on an external surface thereof at locations adjacent the plurality of guide loops. Two ends of a cable are passed alternatively through one of the plurality of guide loops and one of the plurality of tunnel openings, and an adjustable connector connects the two ends and draws them together to tighten the bone sock/sleeve to the bone.

Because of the open-ended design of the bone end containing means, the internal prosthesis of the instant invention, when in place within the residual limb, will permit contact between the bone end and the skin tissue wrapped over the bone end pressure distributing means. Circulation of blood and other body fluids between the bone end and the skin tissue will continue to occur. This circulation will provide nourishment to the bone and help prevent its atrophy.

BRIEF DESCRIPTION OF THE DRAWINGS

The various features, advantages and uses of the present invention will become more apparent by referring to the following detailed description and drawings in which the same numerals refer to like structures throughout the drawings and in which:

FIGS. 9A-9E illustrate different designs of the bone cap of the instant invention employing various combinations of rings and prongs;

FIGS. 10A-10C illustrate various spiral designs of the bone cap of the present invention;

DETAILED DESCRIPTION OF THE PREFERRED EMBODIMENTS

Figure 1:
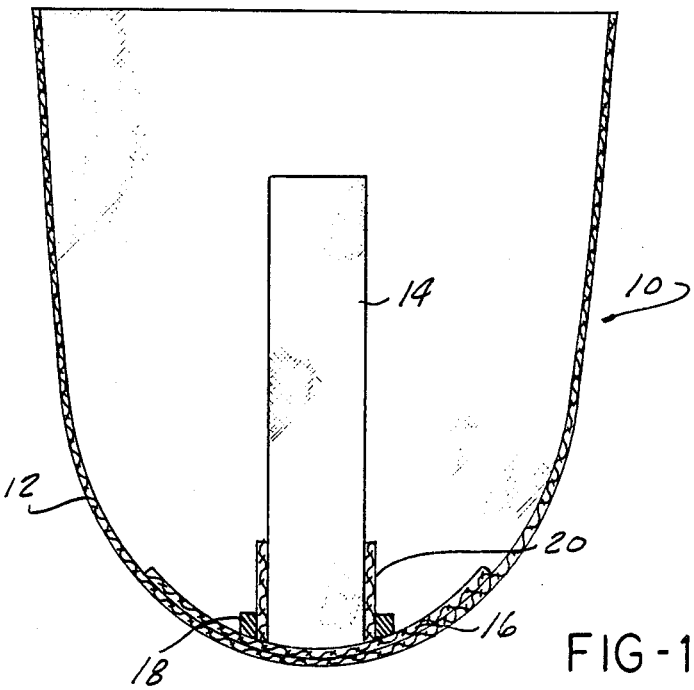
FIG. 1 is a perspective, partially cut away view of one embodiment of the internal prosthesis device of the present invention.

Referring now to FIGS. 1–5, there is illustrated an embodiment of the internal prosthesis of the instant invention. FIG. 1 illustrates this embodiment as it would appear in place on the residual limb (not shown) of an amputee. In FIG. 1, the internal prosthesis 10 is comprised of a large tubular, mesh sock/sleeve 12 which is positioned over the muscle tissue of the residual limb and underneath the skin tissue thereof. Disposed at the center of the large sock/sleeve 12 is a smaller, tubular, mesh bone sock/sleeve 14, sized to receive and surround the free end of the bone of the amputated limb. Large sock/sleeve 12 has a reinforced portion 16 thereof which serves to spread the pressure generated by the end of the bone over the entire bottom surface of the amputated limb. Disposed around the bone sock/sleeve 14 and immediately adjacent the reinforced portion 16 is a support ring 18 which serves to help support the weight of the bone. Optionally, the bone sock/sleeve 14 may have a reinforced section 20 disposed at a portion thereof adjacent the reinforced portion 16 and extending for a distance upward.

Figure 2:
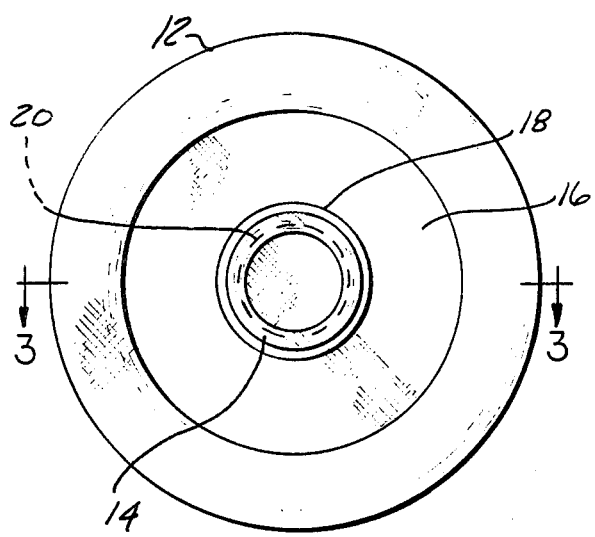
FIG. 2 is a top view of the internal prosthesis device in FIG. 1 showing the two mesh sock/sleeves rolled up preparatory to surgical implant thereof.
Figure 3:
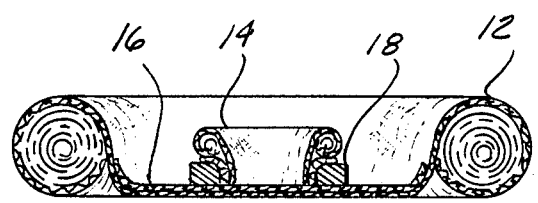
FIG. 3 is a cross-sectional side view of the internal prosthesis device of FIG. 2.

In FIGS. 2 and 3 it is illustrated the internal prosthesis device of FIG. 1, with the two mesh sock/sleeves 12 and 14 being rolled up in the direction indicated by the arrows. The interior prosthesis 10 of FIGS. 2 and 3 is in a pre-surgical condition, and the mesh sock/sleeves 12 and 14 will be unrolled unto, respectively, the muscle and bone tissue of the residual limb when the device is surgically implanted. The bottom of the internal prosthesis 10 will then be covered with flaps of skin from the residual limb.

Figure 5:
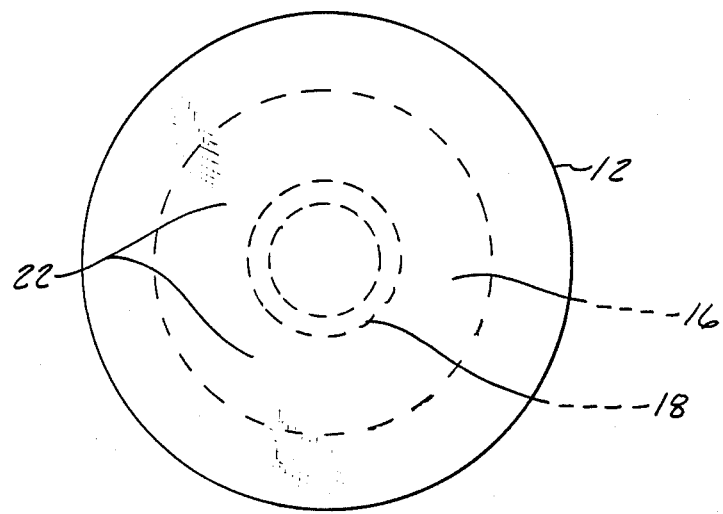
FIG. 5 is a bottom view of an alternative embodiment of the device of FIG. 3 without the support rods.
Figure 4:
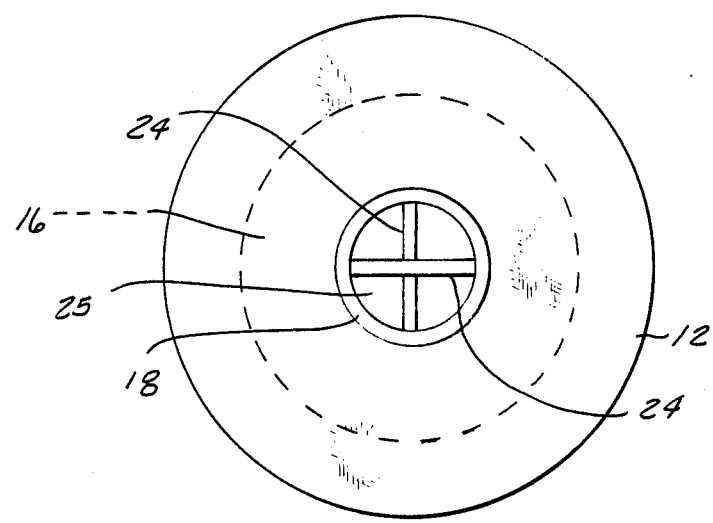
FIG. 4 is a bottom view of the device of FIG. 2 showing support rods disposed within the support ring.

FIGS. 4 and 5 illustrate alternative embodiments of the reinforced portion 16 of internal prosthesis 10 as viewed from the bottom. In FIG. 4, two rods 24 are joined to form an X-shaped cross piece 25 which is integral with a circular piece disposed around the exterior of the bone sock/sleeve 14. Cross piece 25 is disposed interiorly of the bone sock/sleeve 14, with the arms of the X extending therethrough. Alternatively, as illustrated in FIG. 5, the reinforced portion 16 may extend across the bottom of the aperture, and a cross piece may or may not be present in this case. Reinforced portion 16 may be formed of a solid material 22 or alternatively of strengthened mesh material as shown in FIG. 1. In all these various alternative embodiments, the diameter of the reinforced portion 16 should be at least one and one-fourth the diameter of the bone in the residual limb in order to provide an adequate area unto which to diffuse the pressure generated by the bone.

If any portion or all of this internal prosthesis 10 is comprised of a magnetically attractive or receptive material, it may be worn with an external prosthesis which has a correspondingly magnetically attractive or receptive layer disposed in a socket thereof adapted to receive the residual limb. By employing magnetic attraction to help attach the external prosthesis to the residual limb, the external prosthesis will be more secure and have much less tendency to slip, thus providing the user with a more reliable and comfortable prosthesis. Additionally, by employing magnetic attraction to help attach the external prosthesis, many of the straps and other devices employed in the prior art may be eliminated, to the considerable gain in comfort of the user.

At the time of surgical implantation, a fastening means is employed to fasten the bone sock/sleeve 14 to the bone of the residual limb. Typical fastening means include, but are not limited to, adhesives, screws, clamps, pins, staples and combinations thereof. The large, tubular sock/sleeve 12 may be fastened to the muscle tissue and skin of the residual limb by the use of intermittent suture fastening means.

Figure 6:
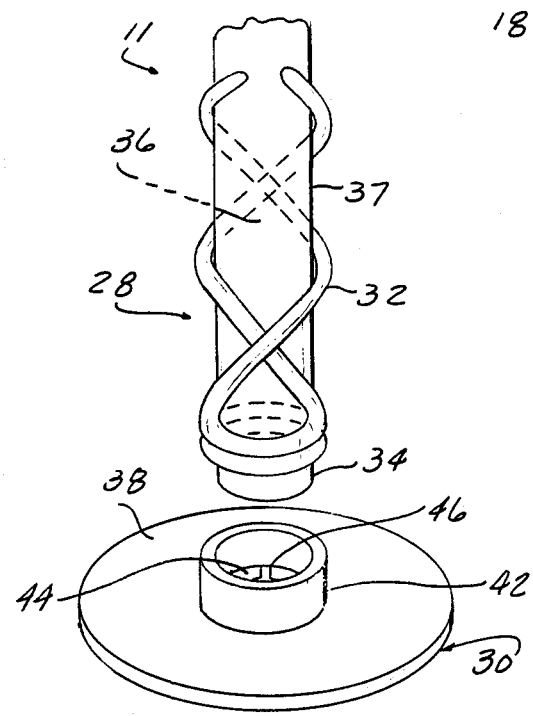
FIG. 6 is a perspective exploded view of another embodiment of the internal prosthesis device of the instant invention, showing the bone cap and plate thereof.
Figure 7:
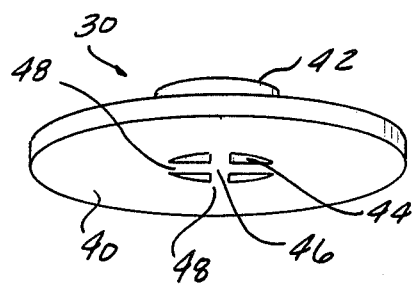
FIG. 7 is a bottom perspective view of the plate of FIG. 6.
Figure 8:
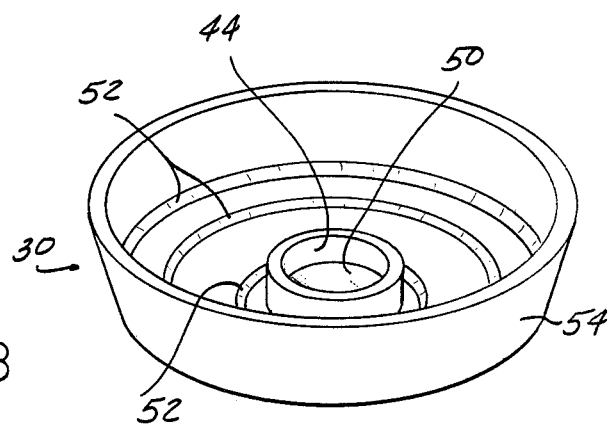
FIG. 8 is a top perspective view of an alternative embodiment of the plate of the instant invention, illustrating a rim and ribs disposed thereon.

FIGS. 6-8 illustrate an alternative embodiment of the internal prosthesis device of the instant invention. In FIG. 6, the bone end containing means 11 comprises a bone cap 28 and the bone end pressure distributing means comprises a plate 30. FIG. 6 depicts the bone cap 28 already in place over a bone 37 of a residual limb. The bone cap 28, which is open at the top end bottom, has first and second side portions 32 and 34, respectively, the second portion 34 having a smaller diameter than the first portion 32. The second portion 34 defines an outwardly extending boss on the cap. The bone cap 28 also comprises an internal cavity 36 sized to receive the end of the bone 37 of the residual limb.

The plate 30 comprises top and bottom surfaces 38 and 40 shown in FIG. 7. An aperture 44 is disposed in the center of the plate 30, and a boss 42 is disposed around the aperture 44 and on the top surface 38. The plate 30 extends radially outward a substantial distance beyond the periphery of the boss 42 to evenly distribute forces from the prosthesis over the end of the residual limb. The plate 30 further comprises support means 46 which are disposed within aperture 44 to support the free end of the bone 37.

FIG. 7 is a bottom perspective view of the internal prosthesis 11 of FIG. 6. In FIG. 7, the support means 46 is comprised of support rods 48 which are disposed within aperture 44 and joined and crossed at their middles, with ends of the rods 48 being integral with the plate 30. In FIG. 8, the support means is comprised of a piece of reinforced mesh 50 which is disposed within the aperture and attached at an edge to the plate 30.

Also depicted in FIG. 8, is an optional rim 54 which is formed integrally on the perimeter of the plate 30 and extends upwardly therefrom. The purpose of rim 54 is to help prevent slippage of the plate 30 with respect to the residual limb when the prosthesis is in place. To the same end, the plate 30 may further comprise a plurality of concentric ribs 62 formed on the plate 30 as illustrated in FIG. 8.

The plate 30, when in place, is disposed completely within the residual limb. During the surgical procedure to attach the device, the bone cap 28 is placed over the end of the bone 37 of the residual limb and bonded thereto. Next, the plate 30 is securely mounted to the cap 28. The skin from one side of the residual limb is then brought down and across the bottom surface 40 of the plate 30 and up to the opposite side and sutured.

If the plate 30 is comprised of a magnetically attracted transmissive material, it may be magnetically attached to an external prosthesis which carries a magnetically transmissive or receptive layer in a socket adapted to receive the residual limb, as described above.

FIGS. 9A-12 illustrate various new designs of the first section 32 of the bone cap of this embodiment of the internal prosthesis of the instant invention. Referring now to FIGS. 9A-9E, there are illustrated designs which employ various combinations of upwardly extending prongs 58, tips 59 and rings 56, 60, and 62.

In FIG. 9A, the first section 32 is comprised of a first ring 56 which encircles the bone end and a plurality of prongs 58 projecting upwardly therefrom, each of the prongs 58 terminating in a tip 59. In FIG. 9B, the tips 59 are inwardly bent to more securely grip the bone. In FIG. 9C, the prongs 58 integrally terminate in a second ring 60 which is disposed in parallel and spaced apart relationship from the first ring 56. In FIG. 9D, the first portion 32 further comprises a non-terminal ring 62 which is disposed around the prongs 58 near the tips 59 thereof. In FIG. 9E, the first portion 32 further comprises a plurality of guide loops 64 formed on the side of the prongs 58 opposite the side adjacent the bone and near the tips 59, a cable 66 whose ends are threaded through the loops and encircle the bone, and an adjustable connector 68 which connects the two ends and draws them together. As the connector 68 draws the ends toegther and tightens the cable, the bone cap is secured to the bone.

FIGS. 10A-10C illustrate various designs of the first portion 32 of the bone cap of this embodiment of the internal prosthesis of the instant invention which employ spirals. In FIG. 10A, the first section 32 comprises a ring 56 and at least one spiral 70 which spirally projects upwardly therefrom to encircle bone 37. In FIG. 10B, two such spirals 70 are depicted, the spirals 70 spiraling in the same radial direction. In FIG. 10C, the two spirals 70 spiral in opposite radial directions.

Figure 11:
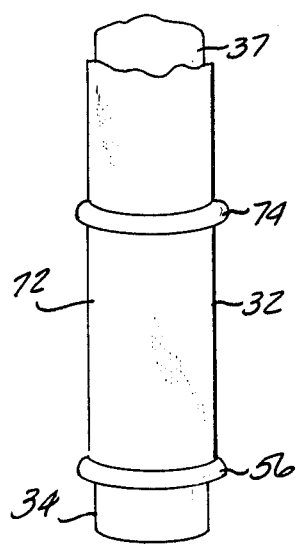
FIG. 11 illustrates an alternative embodiment of the bone cap showing employment of a mesh sleeve.

An alternative design of the first section 32 is illustrated in FIG. 11. First section 32 comprises a ring 56 and a mesh sleeve 72 having an open rolled top 74 and sized to encircle the bone 37. In use, mesh top 74 is fastened to the bone 37 by staples, or other suitable fastening means.

Figure 12:
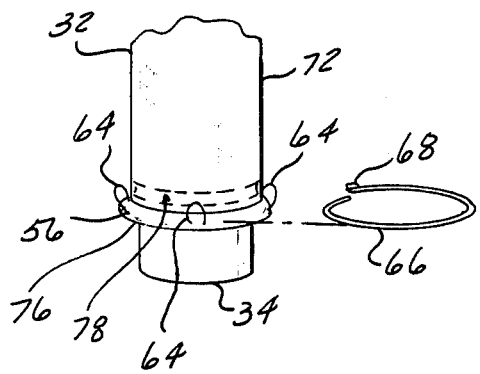
FIG. 12 illustrates another alternative design of the bone cap illustrating loops and cables.

In FIG. 12, yet another design of the first section 32 of the bone cap of one embodiment of the internal prosthesis device of the instant invention is illustrated. In this design, the first portion 32 comprises a ring 56 and a mesh sleeve 72 whose bottom is attached to an internal surface of the first section 32. A plurality of guide loops 64 are disposed around the periphery of the ring 56. A tunnel 76 is formed in the mesh encircling the bone 37 adjacent the ring 56. Tunnel 76 has a plurality of openings 78 formed an internal surface thereof at locations adjacent the plurality of guide loops 64. A cable 66 having two ends passing alternately through one of the plurality of guide loops 64 and one of the plurality of tunnel openings 78 is tightened by an adjustable connector 68 so as to secure the mesh sleeve 72 to the bone 37.

While the invention disclosed herein has been described with reference to certain illustrations and embodiments, it is not intended to be so limited but solely by the claims appended thereto.

I claim:

1. An internal prosthesis for use with a prosthesis attachable externally to a residual limb having a bone with a free end therein, the internal prosthesis comprising:
    bone end pressure distributing means disposed completely within the residual limb;
    open-bottomed bone end containing means attached to the bone end pressure distributing means; means for reinforcing the bone end pressure distributing means; and
    wherein the bone end pressure distributing means comprises a large, flexible, tubular sock/sleeve sized to fit over the muscle tissue of the residual limb and underneath the skin thereof, having a smooth, continuous, reinforced, closed end portion to receive the full force of pressure generated by the free end of the bone.

2. The internal prosthesis of claim 1 wherein the bone end containing means comprises a bone sock/sleeve sized to fit over the free end of the bone disposed at the center of the reinforced portion and integral therewith; and
    a means of permanently fastening the bone sock/sleeve to the bone.

3. The internal prosthesis of claim 2 wherein the tubular sock/sleeve further comprises a support ring having a circular piece disposed around the exterior of the bone sock/sleeve adjacent the reinforced portion and an X-shaped cross-piece integral with the circular piece and disposed interiorly of the bone sock/sleeve, with the arms of the X extending therethrough.

4. The internal prosthesis of claim 1 wherein the large sock/sleeve is comprised of a mesh material.

5. The internal prosthesis of claim 1 wherein the diameter of the reinforced portion is at least one and onefourth the diameter of the bone.

6. The internal prosthesis of claim 4 wherein the reinforced portion is comprised of a strengthened mesh material.

7. The internal prosthesis of claim 4 wherein the reinforced portion is comprised of a solid material.

8. The internal prosthesis of claim 2 wherein the bone sock/sleeve further comprises a reinforced section adjacent to and integral with the reinforced portion and extending upwardly from the reinforced portion.

9. The internal prosthesis of claim 2 wherein the fastening means is selected from the group consisting of adhesives, screws, clamps, pins, staples and combinations thereof.

10. The internal prosthesis of claim 1 further comprising intermittent suture fastening means to fasten the large sock/sleeve to the muscle tissue and skin of the residual limb.

11. The internal prosthesis of claim 1 wherein the bone end containing means comprises:
    a cap securable to the end of the bone, the cap having an open top and bottom, first and second side portions with the second portion having a smaller diameter than the first portion to define an outwardly extending boss on the cap, and an internal cavity formed in the cap sized to fit externally over the free end of the bone.

12. The internal prosthesis of claim 11 wherein the bone end pressure distributing means comprises:
    a plate having top and bottom surfaces, a centrally located aperture formed therein, and a boss formed on the top surface, disposed around the aperture and sized to receive the boss on the bone cap therein, the plate extending radially outward a substantial distance beyond the periphery of the boss to evenly distribute forces from the prosthesis over the end of the residual limb, the plate being disposed completely within the residual limb; and
    support means disposed within the aperture to support the free end of the bone.

13. The internal prosthesis of claim 12 wherein the support means comprises at least two rods joined at their centers with their ends projecting radially outward therefrom and connecting to the plate.

14. The internal prosthesis of claim 12 wherein the support means comprises at least two rods each attached to an end thereof and extending upward and outward therefrom.

15. The internal prosthesis of claim 12 wherein the support means comprises a piece of reinforced mesh attached at an end thereof to the plate.

16. The internal prosthesis of claim 12 further comprising a plurality of concentric ribs formed on the plate.

17. The internal prosthesis of claim 12 further comprising an upwardly extending rim formed integrally on the perimeter of the plate to prevent slippage thereof with respect to the residual limb when the prosthesis is in place.

18. The internal prosthesis of claim 11 wherein the first portion of the bone cap is comprised of a first ring and at least two prongs projecting upwardly therefrom, each of said at least two prongs terminating in a tip.

19. The internal prosthesis of claim 18 wherein each tip is inwardly bent to grip the bone securely.

20. The internal prosthesis of claim 18 wherein the prongs integrally terminate in a second ring disposed in parallel and spaced apart relation to the first ring.

21. The internal prosthesis of claim 18 wherein the first portion further comprises a non-terminal ring disposed around the at least two prongs near the tips thereof.

22. The internal prosthesis of claim 18 wherein the first portion further comprises a plurality of guide loops formed on the side of at the least two prongs opposite the side adjacent the bone and near the tips, a cable whose ends are threaded through the loops and encircle the bone, and an adjustable connector to connect the two ends and draw them together, thereby tightening the cable around the bone and securing the cap thereto.

23. The internal prosthesis of claim 11 wherein the first section further comprises a ring and at least one spiral projecting upwardly therefrom to encircle the bone.

24. The internal prosthesis of claim 23 wherein the prosthesis comprises at least two spirals, each being oriented in a common radial direction.

25. The internal prosthesis of claim 23 wherein the prosthesis comprises at least two spirals, each being oriented in opposite radial directions.

26. The internal prosthesis of claim 11 wherein the first section comprises a ring and a mesh sleeve having an open rolled top and an open bottom sized to encircle the bone, said bottom being attached to an internal surface of a second section and being fastened to the bone at the rolled top a fastening means.

27. The internal prosthesis of claim 11 wherein the first section comprises a mesh sleeve with an open top and bottom sized to encircle the bone, said bottom being attached to an internal surface of the first section, a ring, a plurality of guide loops disposed around the periphery of the ring, a tunnel formed in the mesh encircling the bone adjacent the ring, said tunnel having a plurality of openings formed on an external surface thereof at locations adjacent the plurality of guide loops, a cable having two ends passing alternately through one of the plurality of guide loops and one of the plurality of tunnel openings, and an adjustable connector connecting the two ends and drawing them together to tighten the cable and secure the sleeve to the bone.

28. An internal prosthesis for use with a prosthesis attachable externally to a residual limb having a bone with a free end therein, the internal prosthesis comprising:
   bone end pressure distributing means comprising a magnetic material with which is associated a magnetic field and disposed completely within the residual limb; and
   open-bottomed bone end containing means attached to the bone and pressure distributing means.

* * * * *